US011723631B2

(12) United States Patent
Smadi et al.

(10) Patent No.: US 11,723,631 B2
(45) Date of Patent: Aug. 15, 2023

(54) BRUSH FOR NON-INVASIVE BIOPSY

(71) Applicant: ORLANDO HEALTH, INC., Orlando, FL (US)

(72) Inventors: Yamen Smadi, Orlando, FL (US); Devendra Indulal Mehta, Orlando, FL (US)

(73) Assignee: Orlando Health, Inc., Orlando, FL (US)

( * ) Notice: Subject to any disclaimer, the term of this patent is extended or adjusted under 35 U.S.C. 154(b) by 350 days.

(21) Appl. No.: 16/845,607

(22) Filed: Apr. 10, 2020

(65) Prior Publication Data

US 2021/0315551 A1    Oct. 14, 2021

(51) Int. Cl.
*A61B 10/02*    (2006.01)

(52) U.S. Cl.
CPC ...... *A61B 10/02* (2013.01); *A61B 2010/0216* (2013.01)

(58) Field of Classification Search
None
See application file for complete search history.

(56) References Cited

U.S. PATENT DOCUMENTS

| | | | | |
|---|---|---|---|---|
| 1,711,352 A | * | 4/1929 | Jeffreys | A61B 10/04 606/106 |
| 3,613,664 A | * | 10/1971 | Willson | A61B 10/04 600/569 |
| 4,023,559 A | * | 5/1977 | Gaskell | A61M 25/0074 600/572 |
| 4,136,680 A | * | 1/1979 | Southworth | C12M 33/02 600/572 |
| 4,235,244 A | * | 11/1980 | Abele | A61B 10/04 600/572 |
| 4,586,604 A | * | 5/1986 | Alter | C12M 45/22 604/199 |
| 4,735,214 A | * | 4/1988 | Berman | A61B 10/04 600/572 |
| 4,936,312 A | * | 6/1990 | Tsukagoshi | A61B 10/04 600/564 |

(Continued)

FOREIGN PATENT DOCUMENTS

| WO | WO 2008/091194 A1 | 7/2008 |
|---|---|---|
| WO | WO 2019/139547 A1 | 7/2019 |

OTHER PUBLICATIONS

Partial European Search Report dated Aug. 11, 2021 for European Patent Application No. 21 16 7577 (8 pp.).

(Continued)

*Primary Examiner* — Benjamin S Melhus
(74) *Attorney, Agent, or Firm* — Crowell & Moring LLP

(57) ABSTRACT

A brush for non-invasive biopsy may include a distal tip forming a cavity, where an opening of the cavity faces proximally. A shaft may be included, where the shaft is movable relative to the distal tip, where a distal end of the shaft is located within the cavity when the brush is in a first state, and where at least a portion of the distal end of the shaft is located outside the cavity when the brush is in a second state. A set of bristles may be located at the distal end of the shaft, where the bristles at least partially move from within the cavity of the distal tip to outside the cavity of the distal tip when the brush moves from the first state to the second state.

12 Claims, 4 Drawing Sheets

(56) References Cited

U.S. PATENT DOCUMENTS

| | | | | |
|---|---|---|---|---|
| 4,966,162 | A * | 10/1990 | Wang | A61B 10/04 600/565 |
| 5,129,402 | A * | 7/1992 | Koll | A61B 10/04 600/572 |
| 5,146,928 | A * | 9/1992 | Esser | A61B 10/04 600/569 |
| 5,456,265 | A * | 10/1995 | Yim | A61B 10/0291 600/569 |
| 5,535,756 | A * | 7/1996 | Parasher | A61B 10/02 600/570 |
| 5,738,109 | A * | 4/1998 | Parasher | A61B 10/02 600/585 |
| 5,899,850 | A * | 5/1999 | Ouchi | A61B 10/04 600/104 |
| 6,036,658 | A * | 3/2000 | Leet | A61B 10/0291 600/569 |
| 7,108,661 | B2 * | 9/2006 | Secrest | A61B 10/04 600/562 |
| 8,517,956 | B1 * | 8/2013 | Malanowska-Stega | A61M 25/09 600/565 |
| 10,064,606 | B1 * | 9/2018 | Williams | A61B 10/0096 |
| 11,134,924 | B2 * | 10/2021 | Håkansson | A61B 10/0045 |
| 2003/0208134 | A1 * | 11/2003 | Secrest | A61B 10/04 600/562 |
| 2004/0260199 | A1 * | 12/2004 | Hardia, Jr. | A61B 10/0233 600/569 |
| 2004/0260201 | A1 | 12/2004 | Mueller, Jr. | |
| 2006/0004323 | A1 * | 1/2006 | Chang | A61F 2/186 604/28 |
| 2006/0224041 | A1 * | 10/2006 | Okada | A61B 10/06 600/106 |
| 2009/0018469 | A1 * | 1/2009 | Yanuma | A61B 17/221 600/106 |
| 2009/0299222 | A1 * | 12/2009 | Yanuma | A61B 10/04 600/569 |
| 2010/0136670 | A1 * | 6/2010 | Markovsky | A61B 1/00057 422/68.1 |
| 2010/0234763 | A1 * | 9/2010 | Valdmann | A61B 10/0291 600/569 |
| 2011/0004122 | A1 * | 1/2011 | Sangha | A61B 10/0045 600/572 |
| 2011/0105944 | A1 * | 5/2011 | Ohnishi | A61B 10/0266 600/566 |
| 2012/0253115 | A1 * | 10/2012 | Erin | A61B 10/04 600/104 |
| 2014/0024069 | A1 * | 1/2014 | Figueredo | A61B 10/0291 600/569 |
| 2014/0039346 | A1 * | 2/2014 | Gillespie | A61B 10/0291 600/569 |
| 2014/0276211 | A1 * | 9/2014 | Leahy | A61B 10/04 600/562 |
| 2014/0336528 | A1 * | 11/2014 | Sethi | A61B 10/0266 600/566 |
| 2015/0005665 | A1 * | 1/2015 | Weldon | A61B 1/00131 600/562 |
| 2015/0065915 | A1 * | 3/2015 | Jafri | A61B 10/04 600/569 |
| 2015/0272556 | A1 * | 10/2015 | Lee | A61M 25/0147 600/566 |
| 2015/0320406 | A1 | 11/2015 | Sethi | |
| 2015/0366545 | A1 * | 12/2015 | Irwin | A61B 10/04 600/569 |
| 2016/0047824 | A1 * | 2/2016 | Dilleen | G01N 33/725 205/792 |
| 2016/0331357 | A1 * | 11/2016 | Czarnecki | A61B 10/0291 |
| 2017/0042518 | A1 * | 2/2017 | Sak | A61B 10/0291 |
| 2017/0049422 | A1 | 2/2017 | Ferris | |
| 2018/0078242 | A1 | 3/2018 | Aghdam | |
| 2018/0161021 | A1 * | 6/2018 | Malanowska-Stega | A61B 10/02 |
| 2019/0029653 | A1 * | 1/2019 | Håkansson | A61B 10/0045 |
| 2019/0387961 | A1 * | 12/2019 | Bansal | A61B 1/00133 |
| 2020/0330083 | A1 * | 10/2020 | Alravvi | A61B 10/0291 |
| 2022/0280029 | A1 * | 9/2022 | Nelson | A61B 1/00087 |

OTHER PUBLICATIONS

Extended European Search Report dated Nov. 19, 2021 for European Patent Application No. 21 16 7577.2 (10 pp.).

Y. Smadi et al., "Blind Esophageal Brushing Offers a Safe and Accurate Method to Monitor Inflammation in Children and Young Adults with Eosinophilic Esophagitis," *Diseases of the Esophagus* (*2018*) *0, 1-8*, The International Society for Diseases of the Esophagus, https://academic.oup.com/dote/advance-article-abstract/doi/10.1093/dote/doy056/5037795 (8 pp.).

* cited by examiner

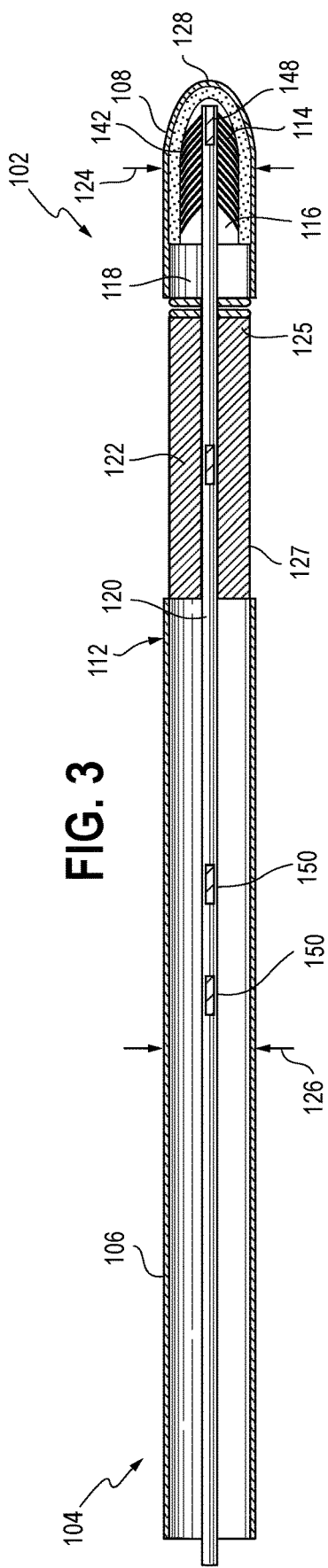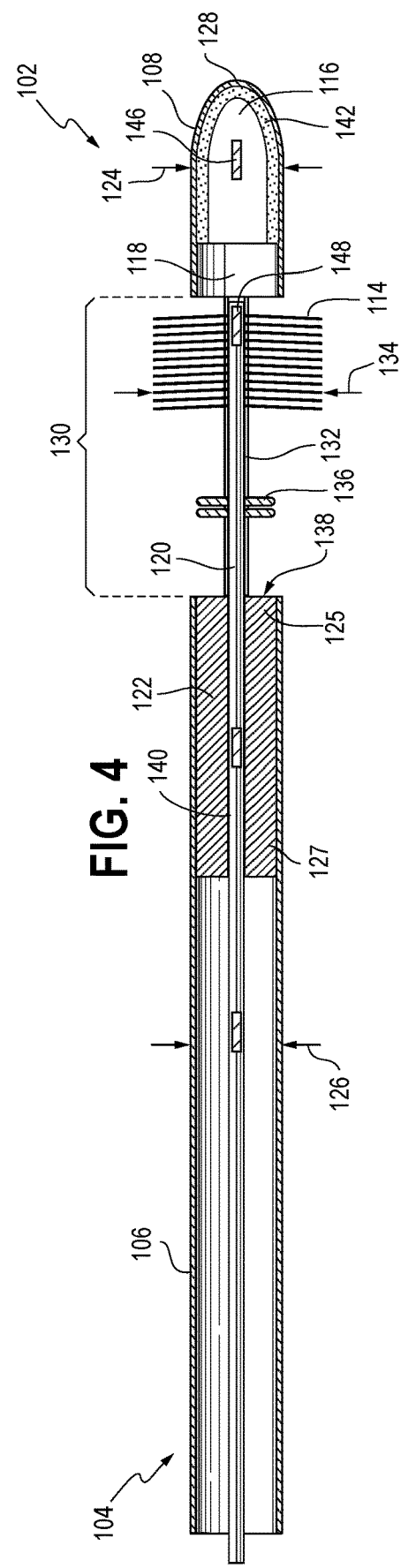

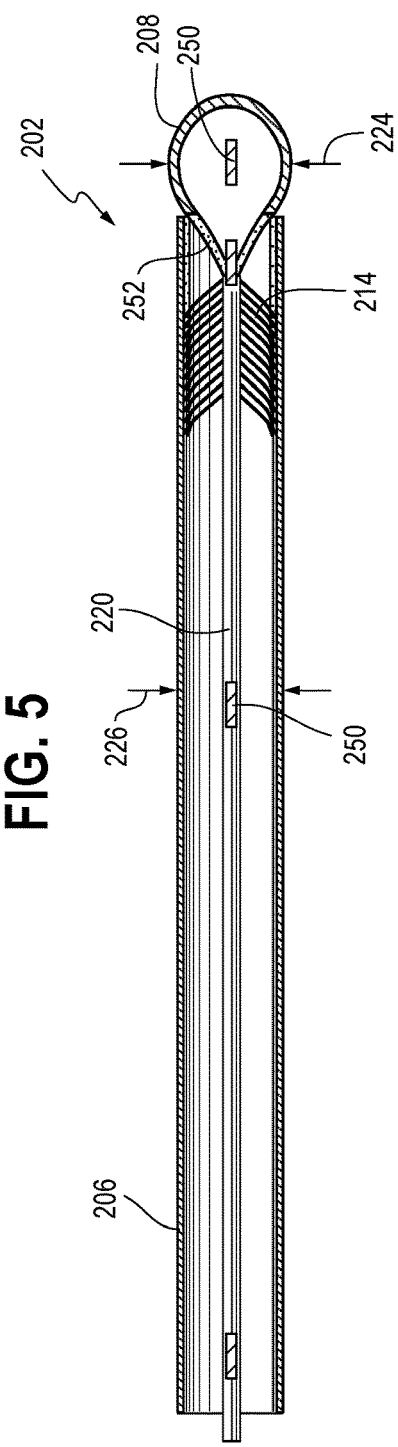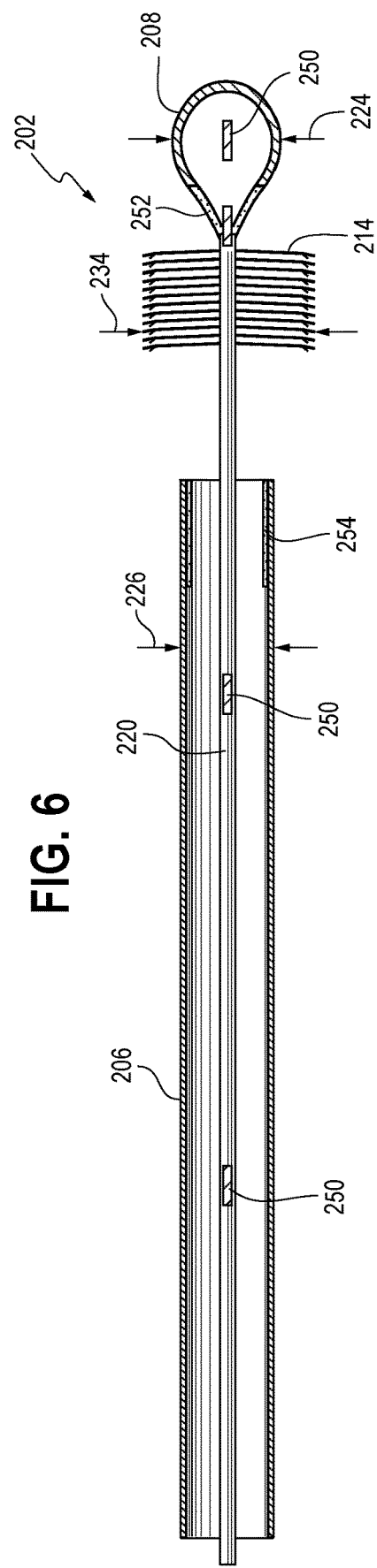

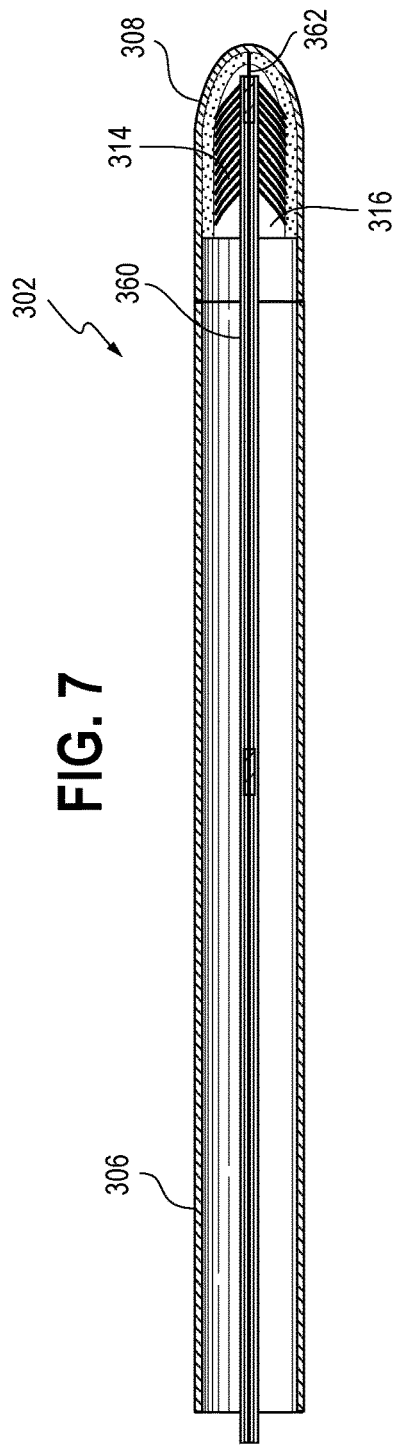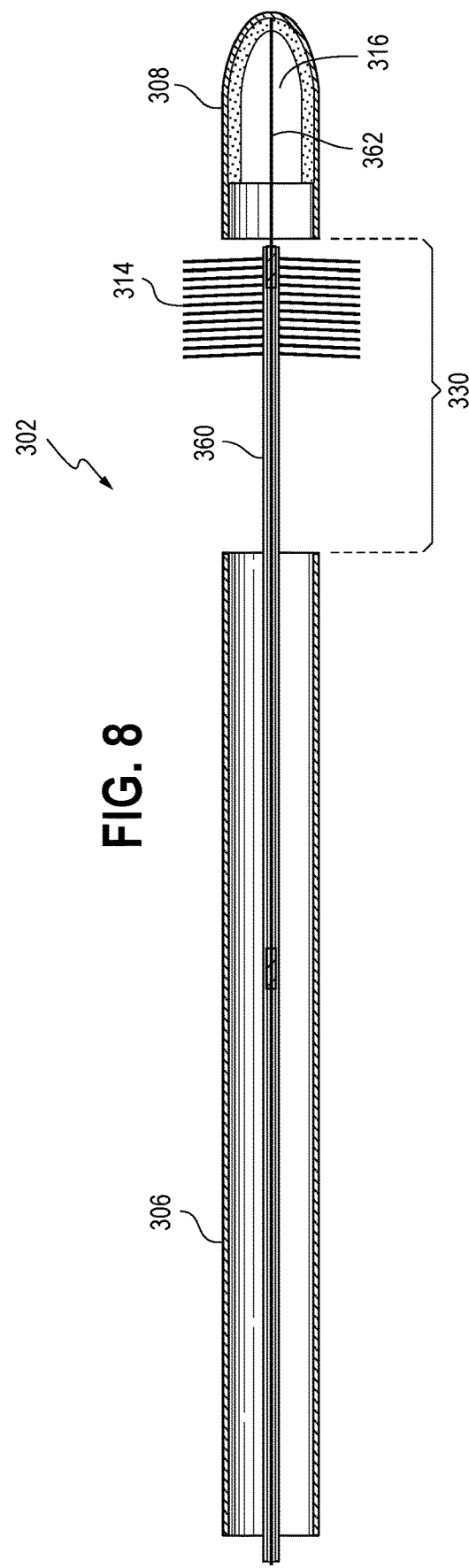

BRUSH FOR NON-INVASIVE BIOPSY

TECHNICAL FIELD

The present disclosure relates to a brush for non-invasive biopsy and related methods of use.

BACKGROUND

Eosinophilic esophagitis (EoE) is a chronic, immune mediated disease characterized clinically by symptoms of esophageal dysfunction and histologically by eosinophil-predominant inflammation. EoE has become a major cause of upper gastrointestinal morbidity in children and adults, with an estimated prevalence between 25.9 and 56.7/100,000 persons in the United States.

Because clinical symptoms provide only a modestly accurate prediction of inflammation in these patients, visual evaluation and biopsies via endoscopy remain the standard methods to monitor disease activity. However, this methodology is challenging, especially in patients who manage the disease via dietary elimination, because an average of 6-11 endoscopies under general anesthesia are required to identify dietary triggers. Further, the disease is patchy and the evaluation by means of light microscopy after hematoxylin and eosin staining of small biopsies might not accurately reflect eosinophil involvement due to degranulation.

In view of the above, there is a critical need for a less invasive, more accurate, and more economical method to monitor the disease. The embodiments of a brush for non-invasive biopsy discussed below addresses these issues.

BRIEF DESCRIPTION OF THE DRAWINGS

The embodiments discussed herein may be better understood with reference to the following drawings and description. The components in the figures are not necessarily to scale. Moreover, in the figures, like-referenced numerals designate corresponding parts throughout the different views.

FIG. 3 is an illustration showing a sectional view of the brush from FIG. 1 in a first (deployment) state in accordance with certain aspects of the present disclosure.

FIG. 4 is an illustration showing a sectional view of the brush from FIG. 1 in a second (operational) state in accordance with certain aspects of the present disclosure.

FIG. 5 is an illustration showing another embodiment of a brush for non-invasive biopsy in a first (deployment) state, where a distal tip of the brush is fixed relative to a set of bristles in accordance with certain aspects of the present disclosure.

FIG. 6 is an illustration showing the brush of FIG. 5 in a second (operational) state in accordance with certain aspects of the present disclosure.

FIG. 7 is an illustration showing another embodiment of a brush for non-invasive biopsy in a first (deployment) state, where a distal tip is movable relative to an elongated sheath and also a set of bristles in accordance with certain aspects of the present disclosure.

FIG. 8 is an illustration showing the brush of FIG. 7 in a second (operational) state in accordance with certain aspects of the present disclosure.

DETAILED DESCRIPTION

The present disclosure relates to a brush for non-invasive biopsy and methods of use. The following embodiments, and variations thereof, provide a less invasive, more accurate, and more economical method for monitoring certain diseases in the human or animal body. For example, the brush embodiments described herein may provide the ability to perform a relatively non-invasive, accurate, and economical method for obtaining a biopsy sample from within the esophagus for evaluating and monitoring eosinophilic esophagitis. Further, unlike other methodologies, the present embodiments may be deployed through the nose and nasal cavity to a target location and then operated from a location outside the body (e.g., at the device's proximal end).

While the specific embodiments described below are tailored towards deployment through the nose for engagement with tissue inside the esophagus, other uses are also contemplated. For example, the non-limiting embodiments described below, and variations thereof, may be used for engagement with any suitable tissue area within a human or animal body.

Figure 1:
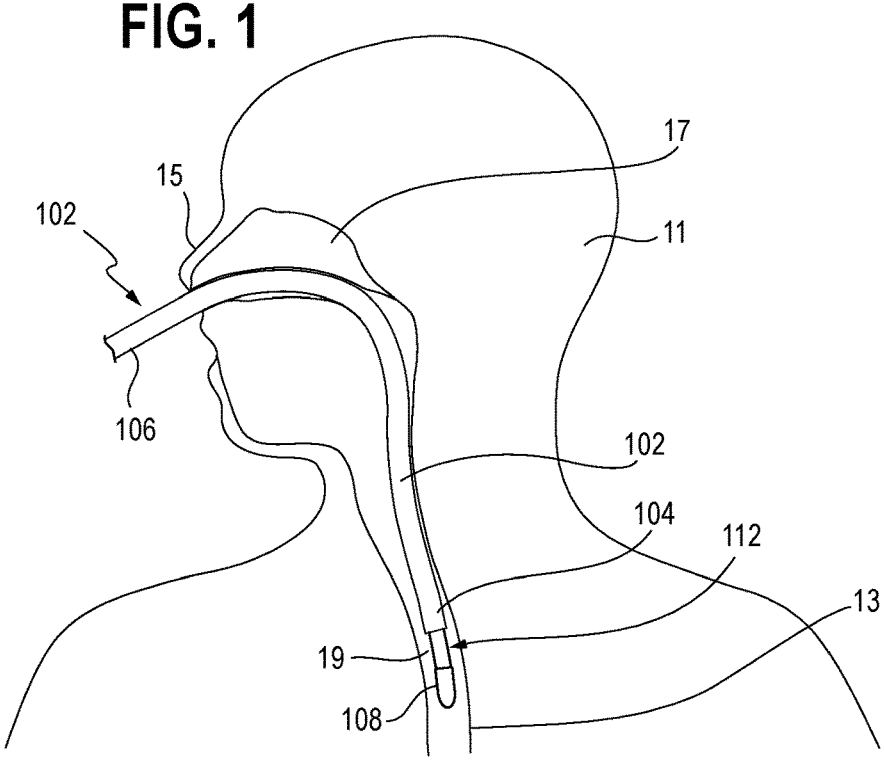
FIG. 1 is an illustration showing a brush for non-invasive biopsy during deployment to a location in the esophagus in accordance with certain aspects of the present disclosure.
Figure 2:
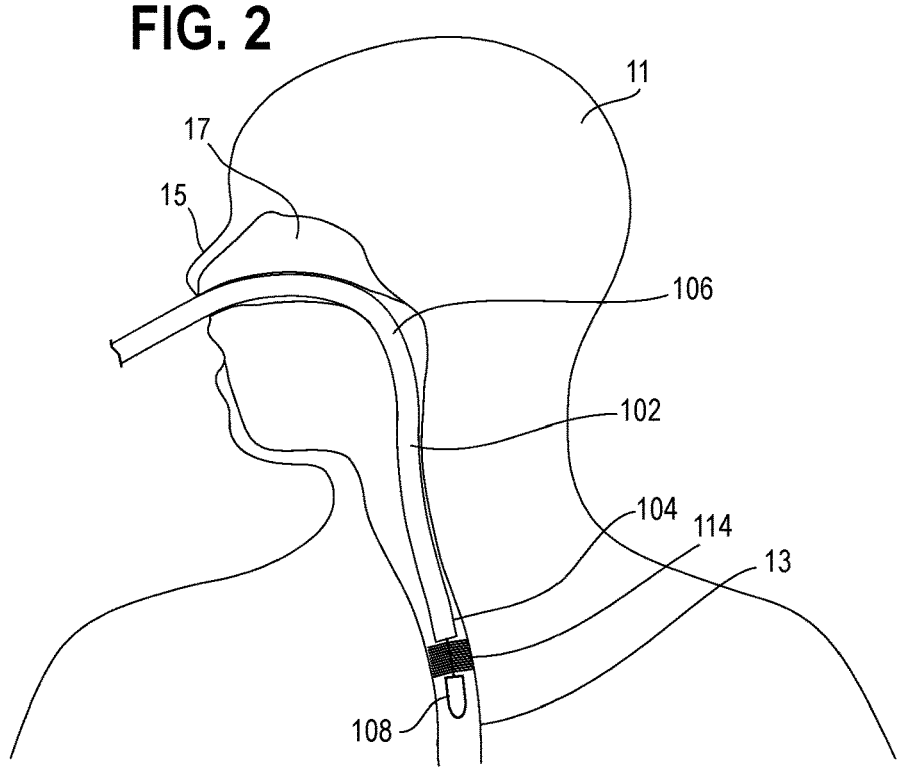
FIG. 2 is an illustration showing the brush of FIG. 1 in an operational state such that a distal end of the brush engages a target tissue area in the esophagus in accordance with certain aspects of the present disclosure.

FIGS. 1-2 show a non-limiting example of a brush 102 for non-invasive biopsy. As discussed above, while any suitable use of the brush 102 may be contemplated, the brush 102 may be specifically configured for collecting a tissue sample within the esophagus 13 (e.g., in performance of an esophageal biopsy during evaluating and monitoring of eosinophilic esophagitis). The brush 102 may include a sheath (e.g., a tube or other elongated device with a cavity therein) that extends the majority of the length of the brush 102. Deployment of the brush 102 to a target site within the esophagus 13 (or another location) may occur by inserting at least the distal end 104 of the brush 102 through the nose 15 and nasal cavity 17, for example. The sheath 106 and components therein may include sufficient flexibility (or another shape-related feature, such as a shape-memory metal) such that it can be guided through the nose 15 and the nasal cavity 17 and into the esophagus 13 without causing damage the surrounding tissue. For example, the tube may be formed of silicon, plastic, or another suitable material.

As shown in FIG. 1, the brush 102 may be deployed in a compacted first state (or deployment state), where the dimensions of the distal end 104 of the brush 102 are relatively small, and where certain components with deformities or discontinuities (e.g., bristles, as discussed below) are sealed within an outer casing such that they do not interfere with the brush's initial deployment. For example, the sheath 106 that extends to a distal end 104 of the brush 102 may primarily form the outer surface areas that contact body tissue when the brush 102 is in the depicted first state.

The distal end 104 of the brush 102 may include the distal tip 108, which may have a taper, a point, and/or other suitable feature for guiding the distal end 104 of the brush 102 to a target location. For example, the taper of the distal tip 108 may act to displace fluids, body tissue, and other particles from the movement path of the brush 102 as the brush 102 moves distally through the body. As discussed below, the distal tip 108 may be fixed to the sheath 106 (e.g., consistent with the embodiment of FIGS. 3-4), or it may be movable relative to the sheath 106 (e.g., consistent with the embodiment of FIGS. 5-6 and the embodiment of FIGS. 7-8). When in the first state of FIG. 1, the outer surface 112 of the sheath 106, distal tip 108, and remainder of the distal end 104 of the brush 102 may be substantially smooth and continuous (e.g., substantially lacking exposed discontinuities on the outer surface) to minimize friction between the brush 102 and surrounding tissue and to prevent damage to said tissue.

When the distal end 104 of the brush 102 is in an appropriate position, the brush 102 may be adjusted to an operational second state shown in FIG. 2. In this second state, certain working features, such as the depicted bristles 114, may be exposed within the body such that they are capable of engaging a target area 19 of body tissue. While not shown in FIGS. 1-2, the brush 102 may include features on its proximal end for controlling adjustment from the first state to the second state, and/or for controlling the working features at the distal end 104 of the brush 102. For example, at least one movable shaft (discussed below) may be engageable by a medical professional on the proximal end of the device. Advantageously, the working components on the distal end of the brush 102 may be operated from a location outside the patient body 11, thereby providing a procedure that is relatively non-invasive relative to other procedures.

FIGS. 3-4 are illustrations depicting a sectional view of the distal end 104 of the brush 102 in the first state and second state, respectively. Referring to FIG. 1, a distal tip 108 of the brush 102 may include a cavity 116, where an opening 118 of the cavity 116 faces proximally. A shaft 120 may be included, which may be fixed to the bristles 114 such that when the shaft 120 moves, the bristles 114 also move. The shaft 120 (and therefore bristles 114) may be movable relative to the sheath 106 and also the distal tip 108. Like the sheath 106, the shaft 120 may be made of a material with sufficient flexibility such that it can bend in an appropriate manner as the distal end 104 of the brush 102 moves through curves within a body cavity. The same is true of other components extending through the sheath 106, if applicable.

Advantageously (and as mentioned above), the brush 102 may be relatively compact in the deployment state (or first state) of FIG. 3, which may facilitate passage through a body cavity during deployment to a target location (e.g., for the evaluation of mucosal inflammation in the esophagus, for example). In this first state, the bristles 114 may be located within the cavity 116 of the distal tip 108 such that they do not interfere with the deployment of the brush 102 as the brush 102 moves through the body towards a target area. In other words, the bristles 114 may be shielded from surrounding body tissue during deployment. To facilitate movement, the outer surface 112 of the brush 102 (including the distal tip 108, the sheath 106, etc.) may be smooth and have a relatively consistent cross-sectional shape and dimension to reduce friction between the outer surface 112 and surrounding body tissue. Further, the outer surface 112 may be substantially continuous (e.g., without discontinuities) to prevent moisture, body tissue, and other unwanted materials from collecting in discontinuities during the deployment procedure.

Further, to provide a substantially continuous outer surface of the brush 102 during deployment, an optional plug 122 may be included. The plug 122 may occupy space that will later be used as working space for movement of the bristles 114 (as discussed below). As shown in FIG. 3, a distal side 125 of the plug 122 may be adjacent to (and potentially in contact with) the distal tip 108, and a proximal side 127 of the plug 122 may be adjacent to (and potentially in contact with) the sheath 106. While not shown in this example, the plug 122 may at extend to a location within the sheath 106 and/or the distal tip 108 in the first state to ensure sufficient contact and/or sealing of the device.

A maximum diameter 124 of the distal tip 108 may be at least as large as an outer diameter 126 of the sheath 106. For example, the maximum diameter 124 of the distal tip 108 may be about the same size as the outer diameter 126 of the sheath 106 (at least at the distal end of the sheath 106). Other areas of the distal tip 108 may have a diameter (or other cross-sectional dimension) that is smaller than the outer diameter 126 of the sheath 106. For example, the distal tip 108 may taper or otherwise reduce its cross-sectional dimension as it moves towards an apex 128 at its distal terminus. This may be advantageous for guiding the brush 102 as it moves through the body, displacing objects in front of the brush 102 to facilitate smooth motion, etc.

To adjust the brush 102 from the first state (of FIG. 3) to the second state (of FIG. 4), the shaft 120 may be retracted in the proximal direction relative to the sheath 106 (which may move the plug 122 to create working space 130 for the bristles 114, as discussed below). Since the sheath 106 is fixed relative to the distal tip 108 (e.g., via a connector 132, which may extend from the sheath 106 to the distal tip 108), such movement also causes the shaft 120 to move in the proximal direction relative to the distal tip 108. When the bristles 114 are fixed to the shaft 120, such action may move the bristles 114 out of the cavity 116 of the distal tip 108 and into the working space 130. A medical professional can then control the movement of the bristles 114 by moving the shaft 120 back-and-forth (e.g., distally and proximally) such that the bristles 114 rub against a target tissue area. Body tissue may thereby be collected by the bristles 114.

As shown, the bristles 114 may include a tendency to expand to a brushing diameter 134 (or uninhibited operational diameter) when the brush 102 is in the second state (of FIG. 4). The brushing diameter 134 of the bristles 114 is defined as the uninhibited diameter of the bristles 114 (i.e., absent contact with a target tissue or another object) when the bristles 114 are located outside the cavity 116 of the distal tip 108. To measure the brushing diameter 134 of the bristles 114, the bristles 114 shall be allowed to expand to their default, uninhibited state at a location outside of a patient body at atmospheric pressure. The brushing diameter 134 is preferably larger the maximum diameter 124 of the distal tip 108 and the outer diameter 126 of the sheath 106. For example, the brushing diameter 134 may be at least 10% larger, such as at least 20% larger, such as at least 30% larger (or more) than the outer diameter of the sheath 106 (and/or the maximum diameter 124 of the distal tip 108. This relative sizing allows the bristles 114 to reach beyond the outer diameter of the sheath 106 such that a target tissue area can be adequately engaged by the bristles 114 for biopsy.

When the plug 122 is included, the shaft 120 may be fixed to a projection 136 that is configured (e.g., sized, positioned, and shaped) to contact a distal surface 138 of the plug 122 when the shaft 120 initially moves in the proximal direction. This contact may cause the plug 122 to move proximally as the shaft 120 moves proximally, resulting in the plug 122 moving into the sheath 106. Advantageously, such movement may provide working space 130 where the bristles 114 may operate. Further, the plug 122 may seal the distal-end opening of the sheath 106 such that it remains free from body fluids and/or other particles. While not shown, the shaft 120 may be fixed to another projection or similar structure, or alternatively a separate device may be included within the sheath 106, for pushing the plug 122 distally into its deployment position after a brushing process is complete.

The plug 122 may include a central channel 140 that is configured (e.g., sized and shaped) for receipt of the shaft 120. Thus, the shaft 120 may extend through the central channel 140. Further, it is contemplated that the plug 122 may be formed from a compressible material such that the central channel 140 compresses around the shaft 120 when the plug 122 is located inside the sheath 106, which may provide a desirable friction on the shaft 120. Advantageously, such friction may enhance the feel to a medical professional and increase the precision of movement when operating the bristles of the brush 102 (e.g., by adding a suitable amount of resistance to the shaft 120).

Optionally, the distal tip 108 may include tissue collection member 142. Without limitation, the tissue collection member 142 may include an absorbent lining or other absorbent feature (such as a sponge-like material or another feature with a characteristic suitable for collecting a tissue sample from the bristles 114), an adherent surface, one or more cavities for receiving and storing body tissue, etc. The tissue collection member 142 may be formed of any suitable material, which may include sufficient absorbency and/or another means of adhering to body tissue and/or fluid in accordance with this description, and it may be used to collect/retain samples which can measured in with any suitable method. For example, the tissue collection member 142 may include a pad of material that absorbs and stabilizes a tissue sample for further processing. Such pads would have a preservative aspect to prevent denaturing of proteins (as understood in the art).

For example, as shown in FIG. 3 (e.g., when the brush 102 is in the first state), the bristles 114 contact a tissue collection member 142 that is located inside the cavity 116 of the distal tip 108. Once the brush 102 is removed from a patient, the collected tissue samples may be obtained from the tissue collection member 142 (and/or the tissue collection member 142 may be removed and evaluated). In certain embodiments, it is contemplated that the tissue collection member 142 may include one or more properties that change based on the composition of the collected tissue sample. For example, the tissue collection member 142 may be configured to react to the presence of a certain biomarker or other chemical, where such reaction provides a visual indication to providing information to the medical professional (e.g., by changing colors).

The brush 102 may include one or more tracking devices configured to indicate a location of the distal tip 108. Without limitation, suitable tracking devices may include magnets that are identifiable in real-time via radiology (e.g., x-ray, ultrasound, or the like) and/or another type of tracking system. For example, referring to FIG. 4, a first tracking device 146 may be located at the distal tip 108, and a second tracking device 148 may be located on the shaft 120. Advantageously, since the shaft 120 is fixed to the bristles 114, such an embodiment may provide real-time information to a medical professional regarding the relative positions of the bristles 114 and the distal tip 108, which may aid in a biopsy procedure. Additional tracking devices 150 may be included at any suitable location for verification purposes, for detection by more than one type of instrument, etc.

FIGS. 5-6 shows another embodiment of a brush 202 for collecting a tissue sample from a patient body. The brush 202 is similar to the embodiment shown in FIGS. 3-4, but it lacks a distal tip having a cavity for receiving a set of bristles 214, and its distal tip 208 is fixed to a shaft 220 that is also fixed to a set of bristles 214. For example, the distal tip 208 shown in FIGS. 5-6 is located at a distal end of a shaft 220. The bristles 214 are located on the shaft 220 (e.g., also fixed relative to the shaft) at a location that is proximal of the distal tip 208. Accordingly, the securement area 221 between the distal tip 208 and the shaft 220 may be fixed relative to where the bristles 214 are secured to the shaft 220.

In the depicted embodiment, a sheath 206 is movable at least in a proximal direction relative to the distal tip 208. The bristles 214 may be at least partially located in the sheath 206 when the brush 202 is in a first state or deployment state (e.g., shown in FIG. 5). The bristles 214 may include a tendency to expand to a brushing diameter 234 when the sheath 206 is in a second state (or operational/brushing state), as shown in FIG. 6. When released from the sheath 206 a brushing diameter 234 of the bristles 214 may be larger than an outer diameter 226 of the sheath 206, thereby allowing the bristles 214 to make sufficient contact with a target tissue are during operation. To operate the bristles 214 of the brush 202, the shaft 220 may be moved back-and-forth (e.g., distally and proximally), perhaps controlled from the proximal end of the device (not shown), such that the bristles 214 rub against the target tissue area to collect a tissue sample.

A maximum outer diameter 224 of the distal tip 208 may be at least as large as the outer diameter 226 of the sheath 206 (e.g., at least at the distal end of the sheath 206). As shown, the maximum outer diameter 224 of the distal tip 208 is a cross-sectional dimension that extends in a direction that is perpendicular to the proximal direction. Advantageously, the distal tip 208 with these dimensions may seal the distal-end opening of the sheath 206 to prevent moisture, body tissue, and other unwanted materials from collecting inside the sheath 206 during deployment. Further, the distal tip 208 in the present embodiment includes a hemispherical shape on its distal side, which may displace fluid, tissue, and/or other particles from the desired pathway of the brush 202 as it is moved towards the target tissue area. Other shapes, such as the shape of the distal tip 208 of FIGS. 3-4 (listed as an example only), are also contemplated.

In FIGS. 5-6, the brush 202 includes a first tissue collection member 252 located on the proximal side of the distal tip 208. A second tissue collection member 254 (shown only in FIG. 6) is located within the sheath 206. Both of these tissue collection members are optional (and may be used with any embodiment consistent with the present description, where compatible), and they may be used in different locations in certain other embodiments. The first tissue collection member 252 and/or the second tissue collection member 254 may include any of the aspects (and variations thereof) discussed above with respect to tissue collection member 142 (of FIGS. 3-4), for example. Thus, the first tissue collection member 252 and/or the second tissue collection member 254 may collect and maintain tissue samples upon contact with the bristles 214 for later analysis by a medical professional.

Like the previous embodiments, the brush 202 may include at least one tracking device 250. For example, at least one tracking device 250 may be fixed to the shaft 220 (e.g., at the distal tip 208, the bristles 214, etc.), which may indicate the location of those components to a medical professional. Additionally or alternatively, at least one tracking device may be fixed to the sheath 206 (not shown in this embodiment). Advantageously, by fixing at least one tracking device to the sheath 206 and at least one tracking device to the shaft 220, the location of each of the components of the brush 202 may be determined.

FIGS. 7-8 show another embodiment of a brush 302 in a first (deployment) state and a second (operational) state, respectively. This embodiment may include any of the features and advantages of the embodiments discussed above (and variations thereof), where compatible. In this embodiment, a sheath 306, a set of bristles 314, and a distal tip 308 are all movable relative to each other (but may otherwise be similar to previously-described corresponding components). For example, like previously-described embodiments, a first shaft 360 may be fixed to a set of bristles 314 and may be movable relative to the sheath 306 to move the bristles 314 during a tissue collection procedure. The distal tip 308 may be fixed to a second shaft 362, which may optionally be coaxial with the first shaft 360. While other configurations are also possible, the depicted first shaft 360 is hollow such that it includes an opening extending longitudinally therethrough, and the second shaft 362 extends through this opening. Thus, moving the second shaft 362 distally relative to the first shaft 360 causes the distal tip 308 to move distally relative to the bristles 314.

To operate the brush 302 (once it is deployed to an appropriate position), the distal tip 308 may move away from the sheath 306 to create working space 330 for the bristles 314 (either by moving the distal tip 308 distally, retracting the sheath 306 proximally, or both). Afterwards (or simultaneously), the first shaft 360 may be moved proximally relative to the distal tip 308 such that the bristles 314 are withdrawn from a cavity 316 of the distal tip 308. In other embodiments, the bristles 314 may initially be within the sheath 306, and therefore moving the bristles 314 into the working space 330 may occur when the bristles 314 are moved distally relative to the sheath 306. Once the bristles 314 are in the working space 330 (e.g., in an expanded state for suitable tissue contact), the bristles 314 may operate in accordance with the embodiments discussed above and variations thereof.

While various embodiments have been described, it will be apparent to those of ordinary skill in the art that many more embodiments and implementations are possible. Accordingly, the embodiments described herein are examples, not the only possible embodiments and implementations.

The subject-matter of the disclosure may also relate, among others, to the following aspects:

A first aspect involves an embodiment of a brush for non-invasive biopsy, and variations thereof. Without limitation, the brush may include one or more of the following features: a distal tip forming a cavity, where an opening of the cavity faces proximally; a shaft that is movable relative to the distal tip, where a distal end of the shaft is located within the cavity when the brush is in a first state, and where at least a portion of the distal end of the shaft is located outside the cavity when the brush is in a second state; and a set of bristles located at the distal end of the shaft, where the bristles at least partially move from within the cavity of the distal tip to outside the cavity of the distal tip when the brush moves from the first state to the second state.

In a second aspect, the brush of the first aspect may further include an outer sheath, where the shaft extends through the outer sheath, and where a maximum diameter of the distal tip is at least as large as an outer diameter of the outer sheath.

In a third aspect, the brush of the second aspect may be configured such that the distal tip may at least partially seals a distal-end opening of the outer sheath when the brush is in the first state.

In a fourth aspect, the brush of any of the second through third aspects may further include a plug located at a distal end of the outer sheath, where the plug at least partially seals a distal-end opening of the outer sheath, and where the shaft extends through an opening of the plug.

In a fifth aspect, the brush of the fourth aspect may be configured such that at least a portion of the plug retracts into the outer sheath when the brush moves from the first state to the second state.

In a sixth aspect, the brush of the fifth aspect may be configured such that a projection fixed to the shaft is configured to contact a distal surface of the plug to provide a force for retracting the plug into the outer sheath when the brush moves from the first state to the second state.

In a seventh aspect, the brush of any of the second through sixth aspects may be configured such that the bristles include a tendency to expand to a bristle diameter when the brush is in the second state, and where the bristle diameter is larger the maximum diameter of the distal tip and the outer diameter of the outer sheath.

In an eighth aspect, the brush of any of the second through seventh aspects may be configured such that a tissue collection member is located inside the outer sheath, where the tissue collection member includes an absorbent material configured to collect and retain a tissue sample upon contact with at least one of the bristles.

In a ninth aspect, the brush of any of the first through eighth aspects may be configured such that the distal tip includes tissue collection member located inside the cavity, where the tissue collection member includes an absorbent material configured to collect and retain a tissue sample upon contact with at least one of the bristles.

In a tenth aspect, the brush of any of the first through ninth aspects may be configured such that the distal tip includes a taper having an apex at a distal terminus of the brush.

An eleventh aspect involves another embodiment of a brush for non-invasive biopsy. Without limitation, the brush may include the following features: a distal tip located at a distal end of a shaft, where a set of bristles is located on the shaft at a location that is proximal of the distal tip; and an outer sheath that is movable in a proximal direction relative to the distal tip, where the bristles are at least partially located in the outer sheath when the brush is in a first state, where the bristles include a tendency to expand to a brushing diameter when the outer sheath is in a second state, and where the brushing diameter is larger than an outer diameter of the outer sheath.

In a twelfth aspect, the brush of the eleventh aspect is configured such that an outer diameter of the distal tip is at least as large of the outer diameter of the outer sheath, and where the outer diameter of the distal tip extends in a direction that is perpendicular to the proximal direction.

In a thirteenth aspect, the brush of any of the eleventh through twelfth aspects is configured such that the distal tip at least partially seals a distal opening of the outer sheath when the brush is in the first state.

In a fourteenth aspect, the brush of any of the eleventh through thirteenth aspects is configured such that the distal tip includes a magnetic tracking device configured to indicate a location of the distal tip.

In a fifteenth aspect, the brush of any of the eleventh through fourteenth aspects is configured such that a tissue collection member is located inside the outer sheath, where the tissue collection member includes an absorbent material configured to collect and retain a tissue sample upon contact with at least one of the bristles.

In a sixteenth aspect, the brush of any of the eleventh through fifteenth aspects is configured such that the distal tip includes tissue collection member, where the tissue collection member includes an absorbent material configured to collect and retain a tissue sample upon contact with at least one of the bristles.

A seventeenth aspect involves another embodiment of a brush for non-invasive biopsy. Without limitation, the brush may include one or more of the following features: a first shaft for controlling a position of a set of bristles, where the set of bristles is fixed relative to the first shaft; a second shaft for controlling a position of a distal tip of the brush, where the distal tip is fixed relative to the second shaft, and where the distal tip forms a distal terminus of the brush; and an outer sheath, where the first shaft extends through the outer sheath, and where the second shaft extends through the outer sheath, where the first shaft and the second shaft are each movable relative to the outer sheath such that the bristles are movable relative to the outer sheath and the distal tip is movable relative to the outer sheath.

In an eighteenth aspect, the brush of the seventeenth aspect is configured such that the distal tip includes a cavity for receiving at least one bristle of the set of bristles.

In a nineteenth aspect, the brush of any of the seventeenth through eighteenth aspects is configured such that a tissue collection member is located inside the cavity of the distal tip, where the tissue collection member includes an absorbent material configured to collect and retain a tissue sample upon contact with at least one of the bristles.

In a twentieth aspect, the brush of the seventeenth aspect is configured such that the first shaft and the second shaft are coaxial.

In addition to the features mentioned in each of the independent aspects enumerated above, some examples may show, alone or in combination, the optional features mentioned in the dependent aspects and/or as disclosed in the description above and shown in the figures.

We claim:

1. A brush for non-invasive biopsy, comprising:
a distal tip forming a cavity,
wherein an opening of the cavity faces proximally;
a shaft that is movable relative to the distal tip,
wherein a distal end of the shaft is located within the cavity when the brush is in a first state,
and wherein at least a portion of the distal end of the shaft is located outside the cavity when the brush is in a second state;
an outer sheath,
wherein the shaft extends through the outer sheath;
a set of bristles located at the distal end of the shaft,
wherein the bristles are configured to at least partially move from within the cavity of the distal tip to outside the cavity of the distal tip when the brush moves from the first state to the second state,
and wherein the bristles are moveable proximally relative to the distal tip while the distal tip remains fixed relative to the outer sheath when the brush is in the second state;
and a plug located at a distal end of the outer sheath,
wherein the plug at least partially seals a distal-end opening of the outer sheath,
and wherein the shaft extends through an opening of the plug,
wherein at least a portion of the plug is configured to retract into the outer sheath when the brush moves from the first state to the second state.

2. The brush of claim 1, wherein a maximum diameter of the distal tip is at least as large as an outer diameter of the outer sheath.

3. The brush of claim 2, wherein the distal tip at least partially seals the distal-end opening of the outer sheath when the brush is in the first state.

4. The brush of claim 2, wherein the bristles include a tendency to expand to a bristle diameter when the brush is in the second state,
and wherein the bristle diameter is larger the maximum diameter of the distal tip and the outer diameter of the outer sheath.

5. The brush of claim 2, wherein a tissue collection member is located inside the outer sheath,
wherein the tissue collection member includes an absorbent material configured to collect and retain a tissue sample upon contact with at least one of the bristles.

6. The brush of claim 1, wherein a projection fixed to the shaft is configured to contact a distal surface of the plug to provide a force for retracting the plug into the outer sheath when the brush moves from the first state to the second state.

7. The brush of claim 1, wherein the distal tip includes a taper having an apex at a distal terminus of the brush.

8. A brush for non-invasive biopsy, comprising:
a distal tip located at a distal end of a shaft,
wherein a set of bristles is located on the shaft at a location that is proximal of the distal tip;
and an outer sheath that is movable in a proximal direction relative to the distal tip,
wherein the bristles are at least partially located in the outer sheath when the brush is in a first state,
wherein the bristles include a tendency to expand to a brushing diameter when the outer sheath is in a second state,
wherein the brushing diameter is larger than an outer diameter of the outer sheath,
and wherein the distal tip is configured to remain fixed relative to the shaft,
and wherein the distal tip includes a magnet configured to indicate a location of the distal tip.

9. The brush of claim 8, wherein an outer diameter of the distal tip is at least as large as the outer diameter of the outer sheath,
and wherein the outer diameter of the distal tip extends in a direction that is perpendicular to the proximal direction.

10. The brush of claim 8, wherein the distal tip at least partially seals a distal opening of the outer sheath when the brush is in the first state.

11. The brush of claim 8, wherein the distal tip includes a tissue collection member,
wherein the tissue collection member includes an absorbent material configured to collect and retain a tissue sample upon contact with at least one of the bristles.

12. The brush of claim 8, wherein a tissue collection member is located inside the outer sheath,
wherein the tissue collection member includes an absorbent material configured to collect and retain a tissue sample upon contact with at least one of the bristles.

* * * * *